United States Patent [19]

Jones et al.

[11] Patent Number: 4,564,616

[45] Date of Patent: Jan. 14, 1986

[54] ANTI-CANCER QUINAZOLINE DERIVATIVES

[75] Inventors: Terence R. Jones, Sutton; Kenneth R. Harrap, Newdigate; Alan H. Calvert, London, all of England

[73] Assignee: National Research Development Corporation, London, England

[21] Appl. No.: 591,566

[22] Filed: Mar. 20, 1984

Related U.S. Application Data

[60] Division of Ser. No. 435,215, Oct. 19, 1982, Pat. No. 4,447,608, which is a continuation of Ser. No. 214,024, Dec. 8, 1980, abandoned.

[30] Foreign Application Priority Data

Dec. 19, 1979 [GB] United Kingdom ................. 7943715
Feb. 28, 1980 [GB] United Kingdom ................. 8006813

[51] Int. Cl.$^4$ .................. A61K 31/505; C07D 239/84
[52] U.S. Cl. ..................................... 514/260; 544/287
[58] Field of Search ................. 544/287; 424/251; 514/260

[56] References Cited

U.S. PATENT DOCUMENTS 3,471,498 10/1969 Davoll ................................ 544/287
3,472,851 10/1969 Davoll ................................ 544/287

OTHER PUBLICATIONS

Calvert et al., Proceedings of the American Association for Cancer Research 20 24 (Mar. 1979).
Calvert et al., Advances in Tumour Prevention, Detection and Characterization, vol. 5, 1980, pp. 272-283.
Paine et al., British Journal of Cancer 38 180 (Jul. 1978).
Jones et al., British Journal of Cancer, vol. 40, 1979, pp. 318-319.
Bird et al., Molecular Pharmacology, vol. 6, 1970, pp. 573-575.
Scanlon, et al., Proc. Amer. Assoc. Cancer Research, vol. 19, p. 136.
Hynes et al., Journ. Med. Chem., vol. 20, No. 4, 1977, pp. 588-591.
Chen et al., Journ. Med. Chem., vol. 22, No. 5, 1979, pp. 483-491.
Scanlon et al., Molecular Pharmacology, vol. 16, 1979, pp. 261-269.
Calvert et al., European Journ. Cancer, vol. 16, 1980, pp. 713-722.
Jones, European Journ. Cancer, vol. 16, 1980, pp. 707-711.
Jones, Chemalog H-Lites, vol. 4, 1980, p. 2.
Jones, et al., British Journ. Cancer, vol. 42, 1980, p. 172.
Calvert et al., British Journ. Cancer, vol. 42, 1980, pp. 172-173.
Harrap et al., Proc. Amer. Assoc. Cancer Research, vol. 21, p. 259.

Primary Examiner—Glennon H. Hollrah
Assistant Examiner—James H. Turnipseed
Attorney, Agent, or Firm—Murray, Whisenhunt and Ferguson

[57] ABSTRACT

Quinazoline derivatives of formula:

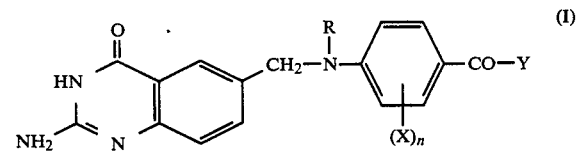

wherein R represents:
(1) a straight or branched chain unsaturated hydrocarbon group, or
(2) a straight or branched chain saturated or unsaturated hydrocarbon group which is substituted by at least one: heteroatom, the or each heteroatom being halogeno when R is a $C_1$ hydrocarbon group; or saturated carbocyclic group; or group containing at least one heteroatom, the or each heteroatom being O, N or S when R contains a cyclic group; and n is 0 or an integer of 1-4;

X or, when n is an integer of at least 2, each X independently, represents a halogeno, $C_1$-$C_4$ alkyl, aryl or aralkyl group or a group including at least one heteroatom; and Abstract continued on next page.

Y represents a group of formula:

$$-NH-CH-COOH \atop |\phantom{-NH-}CH_2-COOH} \quad \text{(L-aspartate)} \quad \text{(a)}$$

$$-NH-CH-COOH \atop |\phantom{-NH-}CH_2-CH_2-COOH} \quad \text{(L-glutamate)} \quad \text{(b)}$$

or $$-NH-CH-COOH \atop |\phantom{-NH-}CH_2-CH_2-CO} -\!\!\left[NH-CH-COOH \atop |\phantom{NH-}CH_2-CH_2-CO\right]_m\!\!-OH \quad \text{(c)}$$

wherein $m \geqq 1$ (poly-L-glutamates);

and the pharmaceutically acceptable salts and esters thereof, which are suitable as anti-cancer agents.

15 Claims, 4 Drawing Figures

ANTI-CANCER QUINAZOLINE DERIVATIVES

This is a divisional application of Ser. No. 435,215, filed Oct. 19, 1982, now U.S. Pat. No. 4,447,608, which in turn is a continuation application of Ser. No. 214,024, filed Dec. 8, 1980, now abandoned.

This invention relates to quinazoline derivatives which are potent anti-tumour (anti-cancer) agents.

The majority of the drugs which have been used to treat tumours have interfered either directly or indirectly with the replication of nucleic acids in the rapidly dividing cells. Many agents, termed antimetabolites, are designed to kill the tumour by depleting its essential growth elements in competing with and displacing the substrates of specific enzymes involved in DNA synthesis. Antimetabolites can be classified according to their specific inhibitory action and examples include analogues of purines and pyrimidines and folic acid antagonists such as aminopterin and amethopterin (methotrexate).

Of the antimetabolites which are folic acid antagonists, methotrexate is used widely in the treatment of human malignant disease, particularly in the treatment of chloriocarcinoma and osteosarcoma and in the maintenance therapy of acute lymphatic leukaemia. Its inhibition of the enzyme dihydrofolate reductase (DHFR, EC 1.5.1.4) causes a depletion of the one carbon-carrying tetrahydrofolate pools, resulting in the inhibition of the de novo synthesis both of thymidine and purine nucleotides necessary for DNA synthesis. Although the "purineless" state induced by methotrexate has been shown to cause toxicity to the gastro-intestinal tract of mice, it does not contribute to the cytotoxic effect of methotrexate against some cultured tumour cell lines and may antagonise it in others. Methotrexate does not require metabolic activation, and does not undergo significant metabolic degradation in the majority of cell types. Known causes of methotrexate resistance include reduced membrane transport and increased cellular DHFR. In this latter case the effective target of methotrexate may become thymidylate synthetase (TS, EC 2.1.1.45), the enzyme catalysing the terminal step in the de novo synthesis of thymidylate required exclusively for DNA synthesis. Direct inhibition of TS may be achieved by an active metabolite of 5-fluorouracil, 5-fluorodeoxyuridine monophosphate. However, 5-fluorouracil resistance is frequently accompanied by a reduction in the appropriate activating enzymes and the drug may also have toxic effects which are attributable to its incorporation into RNA.

There is therefore a requirement for an agent which competes with the tetrahydrofolate cosubstrate of TS rather than the pyrimidine substrate, since such a compound may be expected to have activity equal or superior to methotrexate not only in methotrexate sensitive tumours, but also in those resistant by virtue of raised cellular DHFR. It should also be less toxic to the host since the synthesis of purines would not be affected. Further, folate analogues should be more effective than pyrimidines since they do not require metabolic activation.

Several classical quinazoline antifolates have been shown to be inhibitors of TS, e.g. 2-amino-4-hydroxy and 2,4-diamino derivatives, though while these latter have been shown to be reasonably effective inhibitors of TS they also bind extremely tightly to DHFR.

In accordance with the present invention, it has now been found that enhanced anti-tumour activity can be obtained by substituting certain groups, especially unsaturated hydrocarbon groups, at the 10-position of 2-amino-4-hydroxy quinazoline derivatives. The unsaturated compounds, in particular, inhibit TS to a greater extent than their corresponding saturated analogues, and are thus more efficacious.

Accordingly, the present invention provides a quinazoline derivative of formula:

wherein
R represents:
(1) a straight or branched chain unsaturated hydrocarbon group; or
(2) a straight or branched chain saturated or unsaturated hydrocarbon group which is substituted by at least one: heteroatom, the or each heteroatom being halogeno when R is a $C_1$ hydrocarbon group; or saturated carbocyclic group; or group containing at least one heteroatom, the or each heteroatom being O, N or S when R contains a cyclic group;
n is 0 or an integer of 1–4, preferably 0, 1 or 2
X or, when n is an integer of at least 2, each X independently, represents a halogeno, $C_1$–$C_4$ alkyl, aryl or aralkyl group or a group including at least one heteroatom; and
Y represents a group of formula:

or where $m \geqq 1$ (poly-L-glutamates), preferably 1–9, especially 1;
or a pharmaceutically acceptable salt or ester thereof.

The compounds of the present invention are useful as anti-cancer agents which are either active as such or are suitable as pro-drugs which can be converted in vivo to provide active compounds.

Preferred substituents R as defined under (1) are those containing 2–6 e.g. 4 and particularly 3, carbon atoms and especially those having unsaturation at least in the 2- or in the ω-position. Examples of such groups are alkenyl, alkadienyl, alkynyl and alkadiynyl groups and particular examples are allyl, propargyl, but-2-ynyl, but-3-ynyl and 1-methylprop-2-ynyl.

The groups R as defined under (2) preferably contain up to 6 carbon atoms in the hydrocarbon chain, and particularly up to a total of 4 carbon atoms in the group R as a whole. The saturated hydrocarbon chain preferably contains 1–3 carbon atoms while the unsaturated hydrocarbon chain preferably contains 3 or 4 carbon atoms. There are preferably 1 or 2 substituent groups on the chains. Preferred heteroatom substituents are halogeno, e.g. Cl, Br or F and, in the case of $C_2$ or higher hydrocarbon groups, =O which is preferably attached to a carbon atom other than the α-carbon atom. Examples of such R groups are 2-oxopropyl, formylmethyl, 2,2,2-trifluoroethyl, and 2-chloro-, 2-bromo- or 2-fluoroethyl.

Preferred carbocyclic substituent groups contain 3–6 ring carbon atoms, particularly 3–5. An example of such a group R is cyclopropylmethyl. The carbocyclic ring may itself have at least one $C_1$–$C_4$ alkyl substituent, preferably methyl, of which there are preferably 1–3, particularly 1.

The substituent groups containing at least one heteroatom referred to in definition (2) of R preferably contain 1–6, particularly 1–4, heteroatoms for example halogeno, O, N or S. Particular examples of such groups are OH, $NH_2$, $CONH_2$, COOH and salts and esters thereof, CN, $NO_2$, SH, methylsulphonyloxy, alkoxy and amino acid radicals. Thus, the group R as defined under (2) may be, for example, 2-hydroxyethyl, 3-hydroxypropyl, carbamoylmethyl, 2-aminoethyl, 2-mercaptoethyl, cyanomethyl, carboxymethyl, ethoxycarbonylmethyl, methylsulphonyloxyethyl, dimethylaminoethyl or methoxymethyl.

The heteroatom-containing substituent groups may also contain rings which are either carbocyclic or heterocyclic rings. A particular example of a group including a carbocyclic ring and a heteroatom is phenacyl. Alternatively, the carbocyclic ring may itself be substituted by heteroatom-containing groups, preferably 1–3, e.g. which contain 1–3 heteroatoms which are O, N or S. Particular examples are $C_1$–$C_4$ alkoxy (e.g. methoxy), OH, $NH_2$, COOH, SH, keto, formyl and methylsulphonyloxy. Heterocyclic substituent groups preferably contain 3 to 6 ring atoms, particularly 3, 5 or 6, and the ring heteroatoms, of which there are preferably 1–3, can be N, S or O. An example of such an R group is oxiranylmethyl. These rings may be substituted by at least one $C_1$–$C_4$ alkyl group, preferably methyl, or heteroatom-containing group and preferably by 1 or 2 of these groups. The substitution may be either at a ring carbon atom or heteroatom. These heteroatom-containing groups preferably contain 1–3 heteroatoms, which are O, N or S, and are for example, $C_1$–$C_4$ alkoxy (e.g. methoxy), =O, OH, $NH_2$, COOH, SH and formyl. A particular example of an R group in this category is 5-uracilylmethyl, i.e. a thyminyl group.

The group X as a group containing at least one heteroatom preferably contains 1–3 heteroatoms which may for example be N or O. Particular examples of such groups are $C_1$–$C_4$ alkoxy and $NO_2$. Other preferred groups X are halogeno e.g. chloro, and methyl. The alkyl groups in aralkyl X substituents will usually be 1–4 carbon atoms.

Particularly potent anti-cancer agents in accordance with the present invention are those where R represents propargyl, n=0 and Y represents a glutamic acid radical or a salt or ester thereof. In addition, the corresponding compounds where n=1 and X is chloro or methyl in the 2-position show high activity.

As indicated above, the present invention covers the quinazoline derivatives in the form of their free acids and also in the form of pharmaceutically acceptable salts or esters of these acids, which can be partial salts and esters. Thus, in the case of the compounds containing glutamic acid and aspartic acid radicals, the mono ester mono acid and diester derivatives and corresponding salt forms are also covered. In addition, R groups containing COOH groups for example, can be in salt or ester form e.g. the ethyl ester. The salts of the present invention may be salts formed with physiologically acceptable inorganic or organic acids or bases, and are preferably sodium salts, e.g. disodium salts. The esters are preferably lipophilic esters in which form the compound as a pro-drug may be transported to the enzyme site before being degraded to the corresponding acid form. Examples of preferred esters are those with $C_1$–$C_{20}$ aliphatic groups, e.g. alkyl esters, preferably of 1 to 4 carbon atoms, especially the diethyl ethers.

The compounds of the present invention may be prepared by a partial or complete deprotection process carried out on a compound of formula:

wherein X and n are as defined above, $R^2$ is equivalent to R or is a group R in protected form, $R^1$ is hydrogen or an amino-protecting group and Y' represents a group of formula (a), (b) or (c) as defined above for Y or a salt of said groups or said groups in partially or completely protected form, the protecting group in Y' being an ester group or other protecting group, the compound of formula Ia containing at least one protecting group. If deprotection is carried out to remove more than one protecting group, the deprotections may be carried out simultaneously or in any order.

Thus, for example, the acids and salts of the present invention can be prepared by complete deprotection of a compound of formula Ia, the partial esters can be prepared by deprotection of the 2-amino group and the $R^2$ group as necessary, with Y' either already being in partial ester form or being in completely esterified form which is then partially deprotected and the full esters can be prepared by deprotection of the 2-amino and the $R^2$ group as necessary, with the Y' group in completely esterified form.

Deprotection of the group Y' in ester form to form an acid can, for example, be carried out by mild saponification using a base such as NaOH. The resultant acid may, if desired, subsequently be subjected to reaction with an acid or base to form a pharmaceutically acceptable salt. Most preferably the acid is allowed to react with NaOH to form the corresponding disodium salt. Alternatively, an acid product can be esterified, a salt product can be converted to an acid or ester or an ester product can be transesterified. It may be desirable to form a salt directly from an ester by the deprotection process; where the compound of formula I is in the form of a diester, the disodium salt of the compound of formula I may be formed by saponifying the diester with 3 moles NaOH aq per mole of diester and, when this reaction is complete, adding 1 mole HCl aq per mole of diester and preferably freeze-drying the product salt. Salts can also be formed, e.g. at the 2-amino group, with an acid, such as HCl or HBr.

The particular protecting group $R^1$ will usually be chosen having regard to the nature of the R and $Y'$ groups and the desired product, i.e. such that the conditions required to remove the $R^1$ group will not affect the unprotected R group and will not remove protecting ester groups in $Y'$ where these are required in the final product. An example of an $R^1$ group is the pivaloyl group which can be removed in a saponification step using say NaOH to remove ester groups from $Y'$.

$R^2$ is, as indicated, either equivalent to R or is a desired group R in protected form. Thus, $R^2$ in the latter instance may for example contain the group COOH in ester form, or the group OH protected by an acid group. Examples of such groups $R^2$ are ethoxycarbonylmethyl and 3-acetoxypropyl which are deprotected to carboxymethyl and 3-hydroxypropyl, respectively. These $R^2$ groups may, however, themselves be examples of R. Another example of a protected form of R is where the substituent $R^2$ does not merely contain an extra group, but where it is in a different form from the R group and undergoes conversion as the deprotection step. An example of this is given later where an $R^2$ group 2-hydroxy-3-bromopropyl undergoes a cyclisation reaction under the saponification conditions for removing ester groups from $Y'$ and forms an oxiranylmethyl group R.

The protected compound of formula Ia can itself be prepared by a coupling reaction as follows:

wherein $R^1$, $R^2$, X, n and $Y'$ are as defined for the compound of formula Ia and $X''$ is a leaving group, preferably halogeno, e.g. chloro or bromo, p-toluenesulphonate, methylsulphonate or trifluoromethylsulphonate. This conjugation is generally carried out in the presence of an acid acceptor e.g. calcium carbonate, potassium carbonate, 2,6-dimethylpyridine or triethylamine and in a solvent, e.g. N,N-dimethylacetamide or cellosolve.

The amines of formula II above may be prepared by the direct reaction of a compound of formula $R^2X'$ (where $R^2$ is as defined above and $X'$ is a leaving group, preferably halogeno, e.g. chloro or bromo, p-toluenesulphonate, methylsulphonate or trifluoromethylsulphonate) with N-(4-aminobenzoyl)-L-glutamate, -L-aspartate or -poly-L-glutamate in protected form.

An alternative method for forming the amine of formula II is that of Santi (see J. Heterocyclic. Chem. 4 475) using as starting material a 4-(((4-methylphenyl)-sulphonyl)amino)benzoate ester, e.g. the ethyl ester, which is allowed to react with a compound $R^2X'$ (where $R^2$ and $X'$ are as defined above) to introduce the $R^2$ group onto the amino nitrogen. The ester is then saponified to the free acid, converted to the acid chloride and then coupled with a $Y'$ group in protected, e.g. diester, form. The product is the amine of formula II bearing the protecting group $CH_3$—$\phi$—$SO_2$ on the amino group which can then be removed.

Where it is desired to prepare compounds of the invention containing substituents X, it is preferable to prepare first the corresponding N-(4-nitrobenzoyl)-L-glutamate, -L-aspartate or poly-L-glutamate in protected form containing the appropriate X substituent and to convert that by hydrogenation or reduction to the corresponding 4-amino derivative which is then reacted with $R^2X'$ to form an amine of formula II.

The reactants of formula III above wherein $R^1 = H$ and $X''$ is bromo or chloro may be prepared from the corresponding 6-bromomethyl-2-trimethylacetamido (pivaloyl) compound by reaction in tetrahydrofuran with aqueous HBr and aqueous-methanolic HCl, respectively. N-Bromosuccinimide may be used to effect bromination of the 6-methyl-2-trimethylacetamido-quinazoline.

An alternative method for forming the protected compounds of formula Ia involves reacting the $N^{10}$-unsubstituted conjugated compound in 2-amino protected form and $Y'$ in protected form, with $R^2X'$ (where $R^2$ and $X'$ are as defined above) in accordance with the following scheme:

The compound of formula Ib can itself be prepared by the following reaction:

wherein $X''$ is as defined above. In this reaction, instead of the 6—$CH_2$—$X''$ compound of formula III, it is possible to use the corresponding 6-formyl or 6-cyano compounds since the compound of formula IIa bears no R group on the amino group at this stage of the reaction.

The present invention also provides a pharmaceutical composition which comprises a therapeutically effective amount of an anti-cancer agent as defined for the present invention and a pharmaceutically acceptable carrier or diluent. Experiments using mice having artificially implanted tumours have shown that intraperitoneal injection of anti-cancer agents of the present invention can produce an increase in mean survival time of the mice which is dose related. Further these animals did not lose a significant amount of weight or show other signs of toxicity while undergoing treatment with the drug.

The composition of the invention can, for example, be in a form suitable for parenteral (e.g. intravenous, intramuscular or intracavitary), oral, topical or rectal administration. Particular forms of the composition may be, for example, solutions, suspensions, emulsions, creams, tablets, capsules, liposomes or microreservoirs, especially compositions in sterile injectable form. A further aspect of the present invention thus resides in a method of treating cancer in the human or animal body by administering an anti-cancer agent of the present invention. Therapeutically effective doses in man are considered to be in the range of 50–500 mg/kg body weight.

The compounds of the present invention are anticipated to show a wide range of antitumour activity against leukaemias, lymphoid malignancies and a spectrum of solid tumours, in particular carcinomas and sarcomas. Thus, in addition to their use as single agents, the compounds of the invention could be co-administered with, or contained in a mixed formulation with, for example, mitotic inhibitors (e.g. vincristine, vinblastine), alkylating agents (e.g. cyclophosphamide, melphalan, myleran, chlorambucil, mustine), antimetabolites (e.g. 5-fluorouracil, 6-mercaptopurine, thioguanine, cytosine arabinoside, hydroxyurea), intercalating antibiotics (e.g. adriamycin, bleomycin), or enzymes (e.g. asparaginase).

The compounds of the present invention may also be used as a component of a combined modality treatment, for example including radiotherapy and/or surgery.

The present invention is illustrated by the following Examples.

EXAMPLE 1

Diethyl N-(4-(prop-2-enylamino)benzoyl)-L-glutamate and diethyl N-(4-(prop-2-ynylamino)benzoyl)-L-glutamate were each alkylated with 2-amino-6-chloromethyl-4-hydroxyquinazoline.

A stirred mixture of the chloromethylquinazoline hydrochloride and the amine (1 mol eq.) in 2-ethoxyethanol (2.5 ml per mmol) was heated to 80° C. Triethylamine (2 mol eq.) was then added to give a clear solution which was heated until TLC (10% EtOH-CHCl$_3$/SiO$_2$) indicated maximum (although incomplete) conversion. (Reaction time and temperature were, respectively, 5 hours at 100° C. and 6 hours at 105° C.) The solvent was removed in vacuo and the residue dissolved in CHCl$_3$ and the solution washed with water. The extract was dried (MgSO$_4$) and concentrated to give the crude product. This was purified on silica gel (180 g) by HPLC, eluting with 5% EtOH-CHCl$_3$.

The products were diethyl N-(4-(N-((2-amino-4-hydroxy-6-quinazolinyl)methyl)prop-2-enylamino)benzoyl)-L-glutamate (ester of CB 3716) and diethyl N-(4-(N-((2-amino-4-hydroxy-6-quinazolinyl)methyl)prop-2-ynylamino)benzoyl)-L-glutamate (CB 3721) in the form of non-crystalline gummy solids whose structure was confirmed by elemental analysis and NMR (soln. in DMSO-D$_6$), and the yields and melting points were: ester of CB 3716: 21.5%, 107°–112° C.; CB 3721: 27.5%, 143°–147° C.

EXAMPLE 2

Diethyl N-(4-(N-((2-amino-4-hydroxy-6-quinazolinyl)methyl)prop-2-ynylamino)benzoyl)-L-glutamate, a product of Example 1, was also prepared by the following process.

A solution of 2-amino-6-bromomethyl-4-hydroxyquinazoline hydrobromide (15.1 g) and diethyl N-(4-(prop-2-ynylamino)benzoyl)-L-glutamate (16.2 g) in N,N-dimethylacetamide (300 ml) was stirred over calcium carbonate (13.5 g) for 65 hours at 25° C. The calcium carbonate was removed by centrifugation at 2000 rpm for 15 min, (this can also be removed by filtration through celite). The solvent was then removed at 40° C./0.2 mm. The crude product thus obtained was dissolved in 5% v/v ethanol in chloroform, with the exclusion of a small residue, and chromatographed on silica gel (Merck, Art 15111) eluting with 5% EtOH-CHCl$_3$. The product, diethyl N-(4-(N-((2-amino-4-hydroxy-6-quinazolinyl)methyl)prop-2-ynylamino)benzoyl)-L-glutamate (CB 3721), was an off-white solid mp 146°–148° C. (uncorrected) yield 69%. The structure was confirmed by elemental analysis. Found: C, 62.54; H, 5.65; N, 13.07. C$_{28}$H$_{31}$N$_5$O$_6$ requires C, 63.03; H, 5.86; N, 13.13%.

The starting materials for use in Examples 1 and 2 above may be prepared as follows.

Diethyl N-(4-(prop-2-enylamino)benzoyl)-L-glutamate was prepared by treating diethyl N-(4-amino benzoyl)-L-glutamate (5.00 g) in ethanolic solution (100 ml) for 8 hrs. at 60° C. with allyl bromide (5.4 ml) in the presence of potassium carbonate (2.14 g). Following removal of the solvent in vacuo the residue was dissolved in chloroform and the solution washed with water. The extract was dried (MgSO$_4$) and concentrated to give the crude product. This was purified by HPLC using 50:50 chloroform:petroleum ether as eluant.

To form diethyl N-(4-(prop-2-ynylamino)benzoyl)-L-glutamate, the procedure was repeated except that the reaction was carried out for 4 hours at 70° C. using 10 ml of an 80% solution of propargyl bromide in toluene in place of the allyl bromide.

The structures were confirmed by elemental analysis and NMR spectroscopy and the yields and melting points were: 76.5%, 60°–61° C.; and 55.5%, 98°–99° C., respectively.

EXAMPLE 3

N-(4-(N-((2-amino-4-hydroxy-6-quinazolinyl)methyl)prop-2-enylamino)benzoyl)-L-glutamic acid (CB 3716) and N-(4-(N-((2-amino-4-hydroxy-6-quinazolinyl)methyl)prop-2-ynylamino)benzoyl)-L-glutamic acid (CB 3717) were obtained from the corresponding diethyl esters, which may be prepared as described in Example 1 or 2, by being suspended in 25% EtOH aq. (20 ml per mmol) and treated with 1N NaOH aq. (4 mol eq.). Vigorous shaking gave a solution within 5 min. After 1 hour the solution was clarified by filtration through "Hyflo" and the pH brought to 4.1 using 1N HCl aq. A gelatinous precipitate of the product resulted. It was freed from inorganic ions by three cycles of suspension-centrifugation-decantation. The amorphous, off-white, hygroscopic solid was then dried at 100° C. in vacuo. It was homogeneous by TLC in two systems: (i) n-Butanol:acetic acid:water (5:2:3); (ii) chloroform:methanol:acetic acid (75:20:5).

The structures were confirmed by elemental analysis and UV spectroscopy (spectra determined in 0.1N aq. NaOH). The yield, melting point and UV data were as follows:

CB 3716: yield 46% m.p. 207°–9° C., UV λ (nm)(ε) maxima: 311.5 (29,100), 276 (17,600), 228.5 (49,300), minima: 282 (16,900), 252 (9,060).

CB 3717: yield 81%, m.p. 232°–5° C., UV λ (nm)(ε) maxima: 301.5 (26,600), 279 (23,900), 229 (50,700), minima: 284, (23,700), 251.5 (9,800).

For use, CB 3717 may be formulated at a concentration of 10 mg/ml as the disodium salt at pH 8.5 to 9.0 in a solution of physiological saline (0.9% w/v NaCl).

In Examples 1 and 3 melting points were determined on a Kofler block and are corrected, and elemental analyses for the folate analogues were obtained by the use of both a catalytic additive and an oxygen donor. Every compound had a satisfactory (±0.4%) microanalysis for C, H and N. NMR spectra were taken on a Perkin-Elmer R12B 60 MHz spectrometer except those for the products of Example 1 which were taken at 50° C. on a Bruker HFX 90 MHz Fourier transform instrument. Preparative HPLC was performed on a Jobin-Yvon Chromatospac Prep 10 utilising silica gel (Merck Art 11695), the eluant passing through a Cecil 212A variable wavelength ultraviolet monitor. TLC was performed on Polygram PG 23 precoated silica plates (Macherey-Nagel & Co.). Centrifugation was performed at 20,000 g.

EXAMPLE 4

(a) Diethyl N-(4-(N-((2-amino-4-hydroxy-6-quinazolinyl)methyl)prop-2-ynylamino)benzoyl-L-glutamate (6.436 g.) was suspended in water (130 ml) and treated with 0.1N NaOH$_{aq}$ (36.19 ml, 3.00 mol. equiv.). The mixture was shaken extremely vigorously for 45 min whereupon a solution was obtained. Slight entrained matter was removed by filtration through a grade 3 sinter. After 6 hours from the initial addition of caustic, 0.1N HCl$_{aq}$ (13.00 ml) was added, to give a pH of 8.45. The solution, containing a few specks of precipitated material, was freeze-dried to give a mixture of the disodium salt of N-(4-(N-((2-amino-4-hydroxy-6-quinazolinyl)methyl)prop-2-ynylamino)benzoyl-L-glutamic acid (CB 3717) and sodium chloride as a cream-coloured flaky, amorphous powder. HPLC analysis showed that N-(4-(N-((2-amino-4-hydroxy-6-quinazolinyl)methyl)prop-2-ynylamino)benzoyl-L-glutamic acid (CB 3717) constituted 99% of the organic material.

(b) In another preparation the diethyl ester (14.0 g) was stirred with water (400 ml), ethanol (68 ml) and 0.1N NaOH$_{aq}$ (78.7 ml). After one hour the solution was clarified by filtration and neutralised to pH 8.35 with 0.1N HCl$_{aq}$. The mixture was freeze dried to give a cream coloured solid (15.5 g). Since the mixture is extremely hygroscopic it was allowed to equilibrate with the atmosphere before attempting microanalysis.

Found: C, 43.41; H, 4.03; N, 10.91; Cl, 8.68; Na, 11.53; H$_2$O, 7.69; C$_{24}$H$_{21}$N$_5$O$_6$Na$_2$+1.31 (NaCl)+0.51 (HCl)+2.5 (H$_2$O) (=C$_{24}$H$_{26.51}$N$_5$O$_{8.5}$Na$_{3.31}$Cl$_{1.82}$) requires C, 43.56; H, 4.03; Cl, 9.75; Na, 11.50; H$_2$O, 6.81%. More accurate figures for Cl and H$_2$O were obtained from a separately analysed sample obtained by equilibration of the dry material with the atmosphere for 24 hours—Found: Cl, 9.48; H$_2$O, 7.12%. HPLC analysis of this batch showed that CB 3717 constituted 98% of the organic material.

EXAMPLE 5

A mixture of 2-amino-6-bromomethyl-4-hydroxyquinazoline hydrobromide (1 mol eq.), calcium carbonate (1 mol eq.) and diethyl N-(4-(phenacylamino)-benzoyl)-L-glutamate (1 mol eq.) in N,N-dimethylacetamide (5 ml per mmol) was stirred at room temperature for 60 hrs. The mixture was filtered and the solvent removed in vacuo. The resulting oil was purified by chromatography on silica gel, eluting with 5% methanol-methylene chloride. The product, diethyl N-(4-(N-((2-amino-4-hydroxy-6-quinazolinyl)methyl)-phenacylamino)benzoyl)-L-glutamate (CB 3744) had m.p. 148°–150° C. and was confirmed by elemental analysis and NMR. A second reaction, using 2,6-dimethylpyridine (2 mol eq.) in place of the calcium carbonate, gave an identical product.

In a similar manner, using calcium carbonate as base, the following compounds were prepared by alkylation of the appropriate amine:

| Compound CB No. | R² | X | m | m.p. (°C.) | Footnote |
|---|---|---|---|---|---|
| 3745 | —CH₂COOC₂H₅ | — | 2 | 96–100° | 1 |
|  | —CH₂CONH₂ | — | 2 | 160° (dec) | 2 |
| 3746 | —CH₂CH₂Br | — | 2 | 139–142° | 1,3 |
| 3748 | —CH₂C≡CH | — | 1 | 157–159° | 1,3 |
| 3750 | —CH₂C≡CH | Cl | 2 | 138–141° | 1 |
| 3749 | —CH₂C≡CH | CH₃ | 2 | 162–165° | 1 |
| 3747 | —CH₂CH(OH)CH₂Br | — | 2 | 137–139° | 2,4 |

1 Eluted with 10% methanol-methylene chloride
2 Eluted with 15% methanol-methylene chloride
3 Reaction stirred 100 hours at room temperature
4 Prepared by alkylation of diethyl 4-(3-hydroxy-1-azetidinyl)benzoyl-L-glutamate.

Amine starting materials for use in Example 5 above may be prepared as follows (A)    IIb

CH₂COOC₂H₅
|
R²   CH₂
|    |
HN—⟨benzene⟩—CONH.CH.COOC₂H₅

A mixture of diethyl N-(4-aminobenzoyl)L-glutamate (1 mol eq.), 2,6-dimethylpyridine (1 mol eq.) and ethyl bromoacetate (1 mol eq.) in N,N-dimethylacetamide (2.5 ml. per mmol) was stirred at 90° C. for 5 hours. The mixture was poured into water, extracted with ethyl acetate and the organic phase washed successively with water, 1N sulphuric acid and brine. After drying over-anhydrous sodium sulphate, the solvent was removed in vacuo to give a brown oil which crystallised on trituration with cyclohexane. The product, diethyl N-(4-(ethoxycarbonylmethylamino)benzoyl)-L-glutamate (IIb: R² = —CH₂COOC₂H₅) had m.p. 84°-85° C. and was confirmed by elemental analysis and NMR. In a similar manner the following compounds were prepared by the action of the appropriate alkylating agent on the amine:

| R² | m.p. (°C.) | Footnote |
| --- | --- | --- |
| —CH₂CONH₂ | 167–169° | 1,2,4 |
|  | 135–137° | 1,3,4 |

1 Anhydrous potassium carbonate (0.5 mol eq.) can replace the 2,6-dimethylpyridine in the reaction
2 Stirred at 110° C. for 4 hours
3 Stirred at room temperature for 16 hours
4 Recrystallised from ethanol

(B) 　IIc

A mixture of diethyl N-(4-amino-2-methylbenzoyl)-L-glutamate (1 mol eq.), 2,6-dimethylpyridine (1.1 mol eq.) and propargyl bromide (1.1 mol eq.) in N,N-dimethylacetamide (2 ml. per mmol of the amine) was stirred at room temperature for 16 hours. The mixture was poured into water, extracted with ethyl acetate and the organic phase washed with water, dried over anhydrous magnesium sulphate and the solvent removed in vacuo. The resulting oil was purified by chromatography on silica gel, eluting with 30% ethyl acetate-methylene chloride. The product, diethyl N-(4-(prop-2-ynylamino)-2-methylbenzoyl)-L-glutamate (IIc: R²= —CH₂C≡CH, X= —CH₃, m=2) had m.p. 85°-87° C. and was confirmed by elemental analysis and NMR. In a similar manner the following compounds were prepared by the action of the appropriate alkylating agent on the relevant amine:

| R² | X | m | m.p. (°C.) | Footnotes |
| --- | --- | --- | --- | --- |
| —CH₂C≡CH | Cl | 2 | oil | 1 |
| —CH₂C≡CH | — | 1 | oil | |
| —CH₂CH₂Br | — | 2 | 67–69° (dec) | 2,3 |

¹Eluted with 20% ethyl acetate-methylene chloride
²Used 5 mol eq. of alkylating agent, anhydrous calcium carbonate (3 mol. eq.) in place of 2,6-dimethylpyridine and stirred at 90° C. for 16 hours.
³The aqueous work-up was omitted and after removal of the reaction solvent in vacuo the crude oil was purified on silica gel, eluting with a stepwise gradient of 25% ethyl acetate-hexane to 50% ethyl acetate-hexane.

¹Eluted with 20% ethyl acetate-methylene chloride
²Used 5 mol eq. of alkylating agent, anhydrous calcium carbonate (3 mol. eq.) in place of 2,6-dimethylpyridine and stirred at 90° C. for 16 hours. ³The aqueous work-up was omitted and after removal of the reaction solvent in vacuo the crude oil was purified on silica gel, eluting with a stepwise gradient of 25% ethyl acetate-hexane to 50% ethyl acetate-hexane.

(C) 　IId

A mixture of diethyl N-(4-aminobenzoyl)-L-glutamate (1 mol eq.), calcium carbonate (2.5 mol eq.) and epibromohydrin (5 mol eq.) and N,N-dimethylacetamide (2 ml per mmol of the amine) was stirred at 90° for 40 hours. The mixture was filtered and the solvent removed in vacuo. The resulting oil was purified by chromatography on silica gel, eluting with 25% ethyl acetate-hexane. The product, diethyl 4-(3-hydroxy-1-azetidinyl)benzoyl-L-glutamate had m.p. 87°-90° C. and was confirmed by elemental analysis and NMR.

(D) To a stirred solution of diethyl N-(2-chloro-4-nitrobenzoyl)-L-glutamate in 55% ethanol:water (20 ml per mmol) at room temperature was added sodium hydrogen carbonate (6 mol eq.) followed by the portionwise addition of sodium dithionite (3 mol eq.) over 20 minutes. After stirring for an additional hour the ethanol was removed in vacuo and the residue diluted with brine. The compound was extracted into ethyl acetate and purified by back extraction into 2N hydrochloric acid, neutralisation with sodium bicarbonate, and re-extraction into ether. The ether extract was dried over anhydrous magnesium sulphate and the solvent removed in vacuo to give an oil which crystallised on standing. The product, diethyl N-(2-chloro-4-aminobenzoyl)-L-glutamate, had m.p. 73°-75° C. and was confirmed by elemental analysis and NMR.

(E) Diethyl N-(2-methyl-4-nitrobenzoyl)-L-glutamate in ethanolic solution (8 ml per mmol) was hydrogenated using 10% palladium-charcoal until the theoretical amount of hydrogen had been consumed. The reaction solution was filtered and the solvent removed in vacuo to give an oil which crystallised on standing. The product, diethyl N-(2-methyl-4-aminobenzoyl)-L-glutamate, had m.p. 98°-100° C. and was confirmed by elemental analysis and NMR.

(F) To a stirred suspension of diethyl L-glutamate hydrochloride (1 mol eq.) in toluene (0.5 ml per mmol) cooled to 0° C. was added pyridine (2.5 mol eq.) followed by the dropwise addition of a solution of 2-methyl-4-nitrobenzoyl chloride (1.5 mol eq.) dissolved in toluene (0.7 ml per mmol) over 20 minutes. Stirring was continued for a further 30 minutes at 0° C. and then for 1 hour at room temperature. Following dilution with toluene the mixture was extracted with water, 2N hydrochloric acid, 5% sodium hydrogen carbonate solution and water. The organic phase was dried over anhydrous magnesium sulphate and the solvent removed in vacuo. The resulting oil was purified by chromatography on silica gel, eluting with ethyl acetate-60°-80° C. petroleum ether (1:1). The product, diethyl N-(4-nitro-2-methylbenzoyl)-L-glutamate had m.p. 67°-68° C. and was confirmed by elemental analysis and NMR.

EXAMPLE 6

Diethyl N-(4-(N-((2-amino-4-hydroxy-6-quinazolinyl)methyl)phenacylamino)benzoyl)-L-glutamate (1 mol eq.) was suspended in 33% ethanol-water (40 ml per mmol) and treated with 1N aqueous sodium hydroxide solution (3 mol eq) and the mixture stirred at room temperature for 18 hours. Addition of 0.1N aqueous hydrochloric acid (3 mol eq.) gave a gelatinous precipitate which was purified by six cycles of centrifugation-decantation and resuspension in distilled water. The final aqueous suspension was freeze-dried to give an amorphous white solid. The product, N-(4-(N-((2-amino-4-hydroxy-6-quinazolinyl)methyl)-phenacylamino)benzoyl)-L-glutamic acid (Id: R= no X group, m=2,CB 3733) was confirmed by elemental analysis and proton NMR (solution in DMSO-$d_6$), δ2.0 (2H,m), 2.3 (2H, m), 4.4 (1H,m), 4.7 (2H,s), 5.2 (2H,s), 6.6 (2H,d), 6.5-7.0 (2H,b), 7.2 (1H,d,J 7 Hz), 7.4-7.8 (6H,m), 7.85 (1H,d,J 3 Hz), 8.05 (2H,m) 8.15 (1H,d).

The hydrolysis reaction in the above Example proceeds from the diester via a mono-acid, mono-ester which is not isolated but is hydrolysed in situ to the diacid. In a similar manner the following compounds were prepared by hydrolysis of the appropriate esters:

| Compound CB No. | R | X | m | Footnote |
|---|---|---|---|---|
| 3728 | —CH$_2$COOH | — | 2 | 1,2,7 |
| 3734 | —CH$_2$CONH$_2$ | — | 2 | 8 |
| 3735 | —CH$_2$CH$_2$Br | — | 2 | 3,9 |
| 3737 | —CH$_2$C≡CH | — | 1 | 4,10 |
| 3739 | —CH$_2$C≡CH | Cl | 2 | 4,11 |
| 3738 | —CH$_2$C≡CH | CH$_3$ | 2 | 4,12 |
| 3736 | —CH$_2$CH—CH$_2$ (epoxide) | — | 2 | 5,6,13 |

1 Used 4 equivalents of sodium hydroxide and hydrochloric acid
2 Starting material was the N$^{10}$ ethoxycarbonylmethyl derivative
3 Reaction time 6 hours at room temperature.
4 Used ethanol-water (1:1)
5 Used 4 equivalents of sodium hydroxide
6 Starting material was the N$^{10}$ 2-hydroxy-3-bromopropyl derivative
7 NMR in DMSO-$d_6$ δ2.0(2H,m), 2,3(2H,m), 4.2(2H,s), 4.4 (1H,m), 4.7(2H,s), 6.65(2H,d), 7.1(1H,d,J7Hz), 7.5(1H,dd, J7,3Hz), 7.7(2H,d), 7.8(1H,d,J3Hz), 7.9(1H,d).
8 NMR in DMSO-$d_6$ δ 2.05(2H,m), 2.4(2H,m), 4.1(2H,s), 4.4(1H,m), 4.7(2H,s), 6.3(2H,b), 6.7(2H,d), 7.15 (1H,d,J7Hz), 7.0-7.4(2H,b) 7.5(1H,dd,J 7,3Hz), 7.7 (2H,d), 7.75(1H,d,J3Hz), 8.1(1H,d).
9 NMR in DMSO-$d_6$ δ 1.9(2H,m), 2.2(2H,m), 3.6-4.0(4H,m) 4.25(1H,m), 4.6(2H,s), 6.3(2H,b), 6.7(2H,d), 7.1(1H, d,J7Hz), 7.3(1H,bd), 7.6(3H,m), 8.1(1H,d),
10 NMR in DMSO-$d_6$ δ 2.7(2H,m), 3.1(1H,t,J1.5Hz), 4.3(2H,d,J1.5Hz), 4.7(3H,m), 6.4(2H,b), 6.85(2H,d), 7.2(1H,d,J7Hz), 7.5(1H,dd,J73Hz), 7.7(2H,d), 7.8 (1H,d,J3Hz), 8.2(1H,d).
11 NMR in DMSO-$d_6$ δ 1.95(2H,m), 2.3(2H,m), 3.2(1H,s), 4.3(3H,m), 4.65(2H,s), 6.5(2H,b), 6.7-6.9(2H,m), 7.15 (1H,d,J7Hz), 7.25(1H,d,J7Hz), 7.5(1H,dd,J7,3Hz), 7.8(1H,d,J3Hz), 8.35(1H,d).
12 NMR in DMSO-$d_6$ δ 2.0(2H,m), 2.3(2H,m), 2.4(3H,s), 3.1(1H,t,J1.4Hz), 4.2(2H,bs) 4.3(1H,m), 4.6(2H,s), 6.1-6.6(2H,b), 6.6-6.8(2H,m), 7.15(1H,d,J7Hz), 7.25 (1H,d,J7Hz), 7.5(1H,dd,J7,3Hz), 7.8(1H,d,J3Hz), 8.1(1H,d).
13 NMR in DMSO-$d_6$ 1.9(2H,m), 2.2(2H,m), 2.5(1H,dd, J5,2Hz), 2.65(1H,t,J5Hz), 3.1(1H,m), 3.3-4.0(2H,m) 4.3(1H,m), 4.6(2H,s) 6.3(2H,b), 6.7(2H,d), 7.1(1H,d, J7Hz), 7.35(1H,bd,J7Hz), 7.6(3H,m), 8.1(1H,d).

EXAMPLE 7

A solution of 6-bromomethyl-4-hydroxy-2-trimethylacetamidoquinazoline (7.5 mM) in N,N-dimethylacetamide (25 ml) containing calcium carbonate (15 mM) suspended therein was prepared at 60° C. A solution of diethyl N-(4-(3-acetoxypropylamino)benzoyl)-L-glutamate (7.5 mM) in N,N-dimethylacetamide (10 ml) was added to the stirred reaction mixture over 90 minutes. After stirring a further 12 hours at 60° C., the reaction mixture was filtered and the filtrate, after the addition of water (10 volumes), was extracted with ethyl acetate. The organic phase was washed with water and the solvent removed in vacuo to give an oil.

The oil was chromatographed on silica gel (Merck 60) using mixtures of methylene chloride and ethyl acetate as eluant. The appropriate fractions were evaporated to dryness under reduced pressure to give an oil. When this product was dried under vacuum a foam-like solid, diethyl N-(4-(N-((4-hydroxy-2-trimethylacetamido-6-quinazolinyl)methyl)-3-acetoxypropylamino)benzoyl)-L-glutamate, was obtained, m.p. 61°-4° C.

The amine starting material for use in Example 7 above may be prepared as follows:

Diethyl N-(4-aminobenzoyl)-L-glutamate (0.02M) and 3-acetoxypropyl bromide (0.02M) were condensed in N,N-dimethylacetamide (20 ml) for 12 hours at 100° C. in the presence of potassium carbonate (0.02M). The product was isolated as in Example 5B and the resulting oil chromatographed on silica gel (Merck 60) using a mixture (2:1) of methylene chloride and ethyl acetate as eluant to provide an oil which crystallised on standing; m.p. 59°-62° C.

EXAMPLE 8

Diethyl N-(4-(N-((4-hydroxy-2-trimethyl acetamido-6-quinazolinyl)methyl)-3-acetoxypropylamino)benzoyl)-L-glutamate (0.74 mM) was hydrolysed using 5 equivalents of aqueous sodium hydroxide solution (0.2N, 18.4 ml) in ethanol (75 ml) at 50° overnight. The product was isolated by the addition of 0.2 aq. HCl to pH 4 and then as Example 6 to give N-(4-(N-((2-amino-4-hydroxy-6-quinazolinyl)methyl)-3-hydroxypropylamino)benzoyl)-L-glutamic acid (CB 3729); m.p. 220° C. (d).

NMR (90 MHz in DMSO-$d_6$): δ 1.7-2.5, a multiplet (6H); δ3.6, a multiplet (4H); δ4.4, a multiplet (1H); δ4.7, a singlet (2H); δ6.5, a broad singlet (2H); δ6.7, a doublet J=8.5 Hz (2H); δ7.2, a doublet J=8 Hz (1H); δ7.5, a doublet of doublets J=1.5,8 Hz (1H); δ7.7, a singlet and doublet (3H); δ8.1, a doublet J=7 Hz (1H).

EXAMPLE 9

A solution of 2-amino-6-bromomethyl-4-hydroxyquinazoline hydrobromide (1.00 g) and diethyl N-(4-(((5-uracilyl)methyl)amino)benzoyl)-L-glutamate (1.00 g) in N,N-dimethylacetamide (20 ml) was stirred over calcium carbonate (0.67 g) for 140 hours at room temperature (23° C.). The calcium carbonate was removed by filtering through celite and the solvent then removed at 45° C./0.05 mm. The crude product thus obtained was dissolved in 20% v/v ethanol in chloroform, with the exclusion of a small residue, and chromatographed on silica gel (Merck, Art 15111) eluting with 20% EtOH—CHCl$_3$. The appropriate fractions were combined and concentrated and the final solvent made over to ethanol by repeated evaporations of added ethanol. The volume was reduced to 50 ml and the resulting white crystals, obtained by centrifugation, were washed by resuspension in ethanol, centrifugation and decantation. Drying (P$_2$O$_5$) gave the impure product (32.7%) as an off-white solid, mp >350° C. with some slight decomposition up to this temperature. NMR spectroscopy showed that the material had the quinazoline, uracil and benzoyl-glutamate moieties in the correct 1:1:1 ratio for the product diethyl N-(4-(N-(2-amino-4-hydroxy-6-quinazolinyl)methyl-N-(5-uracilyl)methyl-amino)benzoyl)-L-glutamate.

The amine starting material used in Example 9 above may be prepared as follows.

Diethyl N-(4-aminobenzoyl)-L-glutamate (3.22 g) was treated in N,N-dimethylacetamide solution (60 ml) for 70 hr. at 23° C. with 5-chloromethyluracil (1.93 g) in the presence of calcium carbonate (3.00 g). The calcium carbonate was removed by filtering through celite and the crude product obtained by removal of the solvent at 40°/0.2 mm. An attempt at purification by partition of the oil between chloroform and water led to the formation of an emulsion-like precipitate in the organic layer. The aqueous layer was decanted and the remaining suspension filtered, the retained white solid being washed with hot ethanol. The combined filtrate and washings were evaporated to dryness. The resulting solid was extracted first with hot chloroform and then with hot dichloromethane to remove some starting amine. The remaining white solid was finally recrystallised from ethanol to yield the product as white microneedles m.p. 183°-200° C. The structure was confirmed by elemental analysis and NMR spectroscopy.

EXAMPLE 10

Diethyl N-(4-(N-(2-amino-4-hydroxy-6-quinazolinyl)methyl-N-(5-uracilyl)methyl-amino)benzoyl)-L-glutamate (0.327 g) was suspended in a mixture of water (7 ml) and ethanol (2 ml) and treated with 1N NaOH aq. (6 mol. eq.) Vigorous shaking gave a solution within 30 min. After a further 1.5 hr. the solution was clarified by filtration and the pH brought to 4.0 using 1N HCl aq. A particulate precipitate of the product resulted. It was freed from inorganic ions by three cycles of suspension-centrifugation-decantation. The amorphous white solid was dried at 40° C. in vacuo, to yield the pure diacid, N-(4-(N-(2-amino-4-hydroxy-6-quinazolinyl)methyl-N-(5-uracilyl)methyl-amino)benzoyl)-L-glutamic acid (CB 3743), as its dihydrate (68%), m.p. 250°-255° C. The structure was confirmed by elemental analysis (C,H,N) and by uv spectroscopy (spectrum determined in 0.1N NaOH aq.). λ(nm) (ε) maxima: 310 (29,200), 276.5(22,000), 230 (50,700); minima: 282.5 (21,500), 251.5 (11.600).

EXAMPLE 11

A solution of 2-amino-6-bromomethyl-4-hydroxyquinazoline hydrobromide (0.420 g) and diethyl N-(4-(2-fluoroethylamino)benzoyl)-L-glutamate (0.370 g) in dimethylacetamide (8 ml) was stirred over calcium carbonate (0.417 g) for 45 hours at room temperature (23° C.). The calcium carbonate was removed by filtering through celite and the solvent then removed at 40°-55° C./0.02 mm. The crude product thus obtained was dissolved in 5% v/v ethanol in chloroform, with the exclusion of a small residue, and chromatographed on silica gel (Merck, Art 15111, 250 g) eluting with 5% EtOH-CHCl$_3$. The product, diethyl N-(4-(N-((2-amino-4-hydroxy-6-quinazolinyl)methyl)2-fluoroethylamino)-benzoyl)-L-glutamate, was a white solid m.p. 115°-120° C. (46.3% ) The structure was confirmed by elemental analysis (C,H,N and F) and by NMR spectroscopy.

The amine starting material used in Example 11 above may be prepared as follows.

Diethyl N-(4-aminobenzoyl)-L-glutamate (3.22 g) was treated in DMF solution (40 ml) for 17 hours at 135° C. with 2-fluoroethyl p-toluenesulphonate (4.36 g) (W. F. Edgell and L. Parts, J. Am. Chem. Soc., 77, 4899,(1955)) in the presence of calcium carbonate (3.00 g). It was necessary to add further reagent (4.36 g) after 2 hours 45 min. The calcium carbonate was removed by filtering through celite and following removal of the solvent in vacuo the residue was dissolved in chloroform and the solution washed with water. The extract was dried (MgSO$_4$) and concentrated to give the crude product. This was purified by HPLC on silica gel (Merck, Art 15111) using 50:50 chloroform:petroleum ether as eluant. White crystals were obtained (11.3%) m.p. 105.5°-106.5° C. The structure was confirmed by elemental analysis (C,H,N and F) and by NMR spectoscopy.

EXAMPLE 12

N-(4-(N-((2-amino-4-hydroxy-6-quinaziolinyl)methyl)2-fluoroethylamino)benzoyl)-L-glutamate (0.206 g) was suspended in a mixture of water (4.5 ml) and ethanol (1 ml) and treated with 1N NaOH aq. (5 mol eq.). Vigorous shaking gave a solution within 5 min. After 2 hr. the solution was clairifed by filtration and the pH brought to 4.0 using 1N HCl aq. A gelatinous precipitate of the product resulted. It was freed from inorganic ions by three cycles of suspension-centrifugation-decantation. The amorphous white solid was dried at 70° C. in vacuo, (m.p. >350° C. with some darkening and slow decomposition from 245° C.) giving N-(4-(N-((2-amino-4-hydroxy-6-quinazolinyl)methyl)2-fluoroethylamino)benzoyl)-L-glutamic acid (CB 3731).

Yield 60.1%. The structure was confirmed by elemental analysis (C,H,N and F) and by uv spectroscopy (spectrum determined in 0.1N NaOH aq.). uv λ(nm) (ε) maxima: 307 (29,200), 275 (19,500), 227.5 (49,700); mimima: 279 (19,200), 250 (9,100).

EXAMPLE 13

To a solution of diethyl N-(4-(N-((2-amino-4-hydroxy-6-quinazolinyl)methyl)amino)benzoyl)-L-glutamate (S. P. Acharya and J. B. Hynes, J. Heterocyclic Chem. 12, 1283 (1975)) (2.111 g) in glacial acetic acid (21 ml) was added paraformaldehyde (0.384 g, 3 mol. equiv.), potassium cyanide (0.832 g, 3 mol equiv.) and anhydrous zinc chloride (2.119 g, 3.65 mol. equiv.). The resulting slurry having been stirred, with the exclusion of moisture, for 16.5 hrs, was partitioned between chloroform and water.

The organic phase was removed, washed with water and dried (MgSO$_4$). Evaporation of the solvent left the crude product as a yellow solid. This was twice chromatographed on silica gel (Merck, Art. 11695) applying it to the column each time in 6% ethanol in chloroform and eluting with this same solvent. The product was yet further purified by passing it down a third silica column (Merck, Art 15111), being applied this time as a coat on silica (Merck, Art 7734) obtained by evaporation of a DMF solution at 70° C. (Traces of DMF were removed by desiccation (P$_2$O$_5$) in vacuo for 48 hr). Elution was with 6% ethanol in chloroform. The product, diethyl N-(4-(N-((2-amino-4-hydroxy-6-quinazolinyl)methyl)-cyanomethylamino)benzoyl)-L-glutamate, was an off-white solid, mp 145°-160° C.

Yield 44%. The structure was confirmed by elemental analysis and by PMR spectroscopy. Found: C, 60.53; H, 5.85; N, 15.86. C$_{27}$H$_{30}$N$_6$O$_6$ requires C, 60.66; H, 5.66; N, 15.72%. That the —CH$_2$CN moiety ($\delta$4.73 s,2H) was attached to N$^{10}$ was confirmed by observing that the signal (d, 2H) from the 3' and 5' protons had shifted from $\delta$6.62 to $\delta$6.95 indicative of electron withdrawal from the bridge region of the molecule.

EXAMPLE 14

Diethyl N-(4-(N-((2-amino-4-hydroxy-6-quinazolinyl)methyl)cyanomethylamino)benzoyl)-L-glutamate (0.108 g) was suspended in a mixture of water (2.5 ml) and ethanol (0.5 ml) and treated with 1N NaOH aq. (3 mol. equiv.). Brief stirring (10 min) gave almost a complete solution. After a further 1.25 hours the slight entrained matter was removed by filtration and the pH brought to 4.1 using 1N HCl aq. A gelatinous prrecipitate of the product resulted. It was freed from inorganic ions by two cycles of suspension-centrifugation-decantation. The pellucid solid product, N-(4-(N-((2-amino-4-hydroxy-6-quinazolinyl)methyl(cyanomethylamino)-benzoyl)-L-glutamic acid (CB 3726) was dried over P$_2$O$_5$, finally at 80° C. in vacuo, mp. none, it resinified between 210° and 250° C. Yield 46%. Elemental analysis: Found: C, 57.89; H, 4.77; N, 17.59. C$_{23}$H$_{22}$N$_6$O$_6$ requires C, 57.74; H, 4.63; N, 17.56%.

The following formulations illustrate pharmaceutical compositions of the invention which may be prepared:

|  | per tablet w/w |
| --- | --- |
| Active compound (micronised) | 83.3% |
| "Avicel" - (microcrystalline cellulose) | 12.7% |
| polyvinylpyrrolidone | 1% |
| alginic acid | 2% |
| magnesium stearate | 1% |

The compound of the invention may be mixed with the "Avicel" and polyvinyl pyrrolidone added, dissolved in sufficient industrial methylated spirits 74° OP to produce a mass suitable for granulating. The mass may be granulated through a 20 mesh sieve (British mesh standard) and the resultant granules dried at a temperature not exceeding 50° C. The dried granules may be passed through a 20 mesh sieve and the alginic acid and magnesium stearate then added and mixed with the granules. The product may be compressed into tablets.

By the same method the following formulation may be prepared:

|  | per tablet w/w |
| --- | --- |
| Active compound | 62.5% |
| "Avicel" (microcrystalline cellulose) | 33.5% |
| polyvinylpyrrolidone | 1% |
| alginic acid | 2% |
| magnesium stearate | 1% |

Further tablets may be of the following composition:

|  | per tablet w/w |
| --- | --- |
| Active compound (micronised) | 83.3% |
| lactose (300 mesh) | 6.3% |
| maize starch | 5% |
| gelatine | 3.3% |
| magnesium stearate | 2% |

These tablets may be prepared by mixing a compound of the invention with lactose and half the total quantity of maize starch required, and adding to the mass a 5% w/v solution of gelatine in water.

The product may be granulated through a 16 mesh sieve, and the resultant granules dried to constant weight at a temperature not exceeding 60° C. The dried granules may be passed through a 20 mesh sieve and mixed with magnesium stearate and the remainder of the maize starch. The product may be compressed into tablets.

An injectable solution may be prepared as follows.

Where the compound of the invention is in acid form, it (2 mmol) may be dissolved in 100 ml of 0.9% NaCl aq. containing sufficient NaOH or other suitable base for its neutralisation.

The compounds of Example 2 were evaluated in vitro as inhibitors of TS and cell growth and in vivo against the L1210 tumour. Since methotrexate (MTX) resistance is an important problem in cancer therapy, the compounds of the present invention were also investigated with this in mind. The cross-resistance of the MTX resistant cell line L1210/R71, which is known to have elevated DHFR but normal MTX transport, was measured in culture, and the ability of the compounds of the invention to compete with labelled MTX or folic acid for transport into L1210 cells was also assessed.

Enzymology

The compounds CB 3716 and CB 3717 were each dissolved in N/10 NaOH and neutralised before use. The cytosol of log phase L1210 cells harvested from animals was partially purified for TS I$_{50}$ and Ki determinations to remove from the preparation a phosphatase which degrades dUMP to deoxyuridine. (The I$_{50}$ was defined as the inhibitor concentration necessary to reduce the reaction rate of TS by 50%). DHFR was purified by affinity chromatography and Ki determinations performed.

The results are shown in the following Table 1 and comparison is made with the 10-propyl compound corresponding to CB 3716 and 3717

TABLE 1

| Compound | R | THYMIDYLATE SYNTHETASE $I_{50}$ (nM) | DIHYDROFOLATE REDUCTASE $K_i$ (nM) |
|---|---|---|---|
| Comparison | —$CH_2$—$CH_2$—$CH_3$ | 170 | 20 |
| CB3716 | —$CH_2$—CH=$CH_2$ | 69 | 27 |
| CB3717 | —$CH_2$—C≡CH | 5 | 14 |

The presence of allyl and propargyl groups at the 10-position as compared with the propyl group gives TS inhibition values which are enhanced approximately 3- and 30- fold respectively, while the inhibition of DHFR remains of the same order. The inhibition of TS by compound CB3717 was characterised and found to be competitive with $N^5,N^{10}$-methylenetetrahydrofolate with a Ki of approximately 1.1 nM.

Cell Culture

L1210 and L1210:R71 cells were grown in continuous suspension culture in RPMI 1640 medium containing 10% horse serum (Flow Laboratories, Irvine, Scotland, UK). Cells were diluted to $10^5$/ml and additions (diluted in medium and sterilised by Millipore filtration) made prior to starting each incubation. Cell counts were performed after 24 and 48 hours using an improved Neubauer haemocytometer. The $ID_{50}$ was defined as that concentration of drug necessary to reduce the 48 hour count to 50% of control.

The $ID_{50}$ concentrations in cell culture for L1210 and L1210:R71 (MTX-resistant) are shown in Table 2 below. Not only did the toxicity of the drugs to both cell lines increase with progressive unsaturation of the 10-substituent but also the degree of cross-resistance of the L1210:R71 became less marked. The L1210:R71 is about 600 fold resistant to MTX.

TABLE 2

| Compound | $ID_{50}$ VALUES ($\mu$m) L1210 | $ID_{50}$ VALUES ($\mu$m) L1210:R71 | CROSS RESISTANCE ($ID_{50}$ L1210:R71/$ID_{50}$ L1210) |
|---|---|---|---|
| Comparison* | 33.0 | 315 | 10 |
| CB 3716 | 8.8 | 100 | 11 |
| CB 3717 | 5.0 | 14 | 3 |

*Compound corresponding to CB 3716 and 3717 in which R = propyl.

Figure 1:
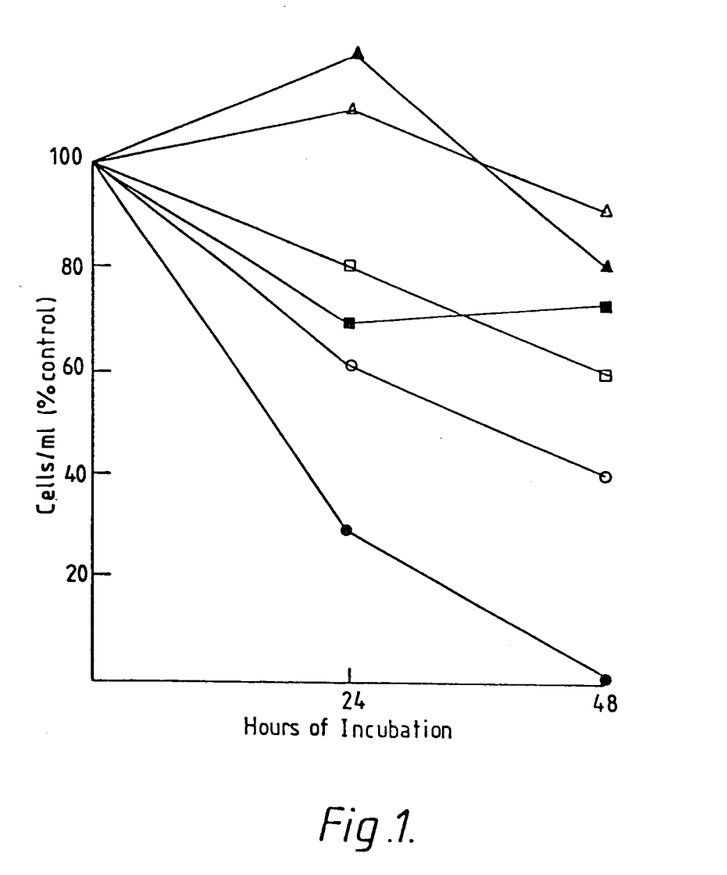

Reversal of the toxicity of compound CB 3717 could be achieved by co-incubation with thymidine (10 $\mu$M) but only partial reversal was achieved with folinic acid at any concentration up to 100 $\mu$M. These results are illustrated in FIG. 1 of the accompanying drawings which shows protection of L1210 cells in culture from 20 $\mu$M CB 3717.

● CB 3717 alone; ○ CB 3717+folinic acid 5 $\mu$M;
□ CB 3717+Folinic acid 50 $\mu$M; ■ CB 3717+folinic acid 500 $\mu$M;
▲ CB 3717+TdR 1 $\mu$M; △ CB 3717+TdR 10 $\mu$M These results indicate that CB 3717 acts on TS as the chief locus in particular since its affinity for DHFR is 10-fold less than that for TS and also since it is possible to afford virtually complete protection to L1210 cells by the addition of thymidine to the medium while the addition of folinic acid does not reverse the effect of the agents even when high concentrations (100 $\mu$m) are used.

Compounds prepared in the other Examples were similarly evaluated in vitro as inhibitors of TS and cell growth with the following results: (in these experiments, the TS used was purified >2,000 fold from L1210 cells by affinity chromatography). [Even where these compounds do not show particularly good TS inhibition, they are of potential interest as anti-cancer agents in that they show toxicity to L1210 cells in tissue culture.]

| CB No. | Ex No | TS $I_{50}$ (nM) | TS $I_{50}$ (CB 3717 as control) | $\frac{(I_{50})x}{(I_{50})}$ CB 3717 (Relative potency) | $ID_{50}$ ($\mu$M) L1210 (Tissue culture) | Reversal by thymidine (in culture) |
|---|---|---|---|---|---|---|
| 3717 | 3,4 | variable 6–48 (see next column) | — | 1 | 6.5–8.5 variation not signif. | yes |
| 3721 | 1,2 | >3,000 | 48 | >62 | 52 | |
| 3726 | 14 | 94 | 6 | 15.6 | 5.4 | |
| 3728 | 6 | 1,400 | 14 | 100 | 27 | yes |
| 3745 | 5 | | | | >100 | |
| 3729 | 8 | 120 | 14 | 8.6 | 54 | |
| 3731 | 12 | 95 | 14 | 6.8 | 16 | |
| 3733 | 6 | 1,640 | 41 | 40 | 100 | |
| 3744 | 5 | | | | >100 | |
| 3734 | 6 | >3,000 | 48 | >62.5 | 87 | yes |
| 3735 | 6 | 1,100 | 48 | 23 | 52 | |
| 3746 | 5 | | | | >100 | |
| 3736 | 6 | 310 | 41 | 7.6 | >300 | |
| 3737 | 6 | 66 | 41 | 1.6 | >100 | |
| 3748 | 5 | | | | 100 | |
| 3738 | 6 | 47 | 41 | 1.1 | 24 | |
| 3749 | 5 | | | | 100 | |
| 3739 | 6 | 30 | 14 | 2.1 | 17 | |
| 3750 | 5 | | | | 18 | |
| 3743 | 10 | 1,000 | 45 | >22 | 4.7 | yes |
| 3747 | 5 | | | | >100 | |

Transport Studies

Transport studies were conducted on compound CB 3717 as representative of the invention compounds by incubating cells in the presence of a labelled substance, removing aliquots, separating and washing the cells by centrifugation and counting the pellet.

Figure 2:
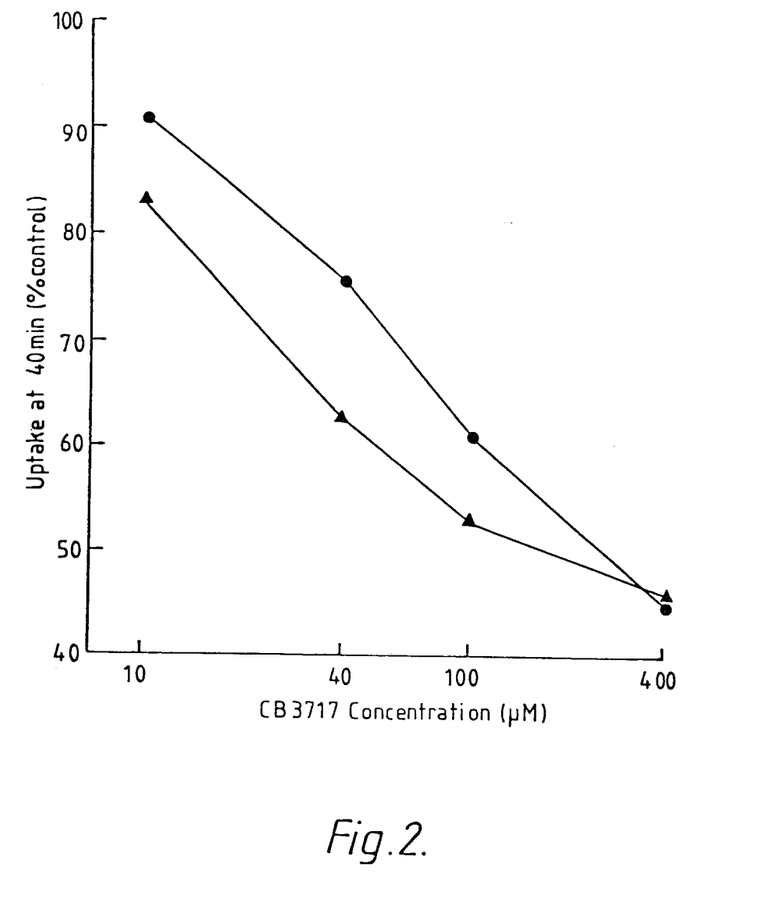

The effect of varying concentrations of compound CB 3717 in the medium upon the transport of tritiated methotrexate and tritiated folic acid is shown in FIG. 2 of the accompanying drawings.

● 4 $\mu$M MTX; ▲ 4 $\mu$M folic acid

The transport of both of these compounds was inhibited by compound CB 3717.

Thus CB 3717, apparently avoids the problems of using methotrexate to which resistance can be built up by an increased cellular DHFR content and a reduction in that cell membrane transport mechanism responsible for carrying both the methotrexate and the tetrahydrofolate derivatives. The cytotoxic locus of CB 3717 is TS and not DHFR and the transport studies show that this compound can apparently be transported by the pathway used for methotrexate and also by that for folic acid since CB 3717 caused a dose-dependent reduction in the transport of both these materials.

Treatment of L1210 Tumour-bearing Animals

The L1210 tumour was carried out routinely in DBA2 mice. For experiments $5\times10^4$ cells were implanted i.p. into female C57B1×DBA2 F1 hybrid mice 3 days prior to treatment, giving an established tumour of about $2\times10^6$ cells at the time of treatment. The compound CB 3717 was dissolved in N/10 NaOH, diluted to the appropriate volume and the pH adjusted to 8.5 before i.p. injection.

The results are summarised in Table 3 which follows:

TABLE 3

THERAPEUTIC RESULTS OF CB 3717 TREATMENT IN MICE BEARING THE L1210 ASCITIC TUMOUR
The bracketed groups indicate individual experiments

| Compound CB 3717 dose (mg/kg) | Animals per group | Protocol | % Increase in mean survival time | Long term survivors (>200 days) |
|---|---|---|---|---|
| 80 | 5 | single dose | 14 | 0 |
| 160 | 5 | single dose | 32 | 0 |
| 8 | 5 | daily × 5 | 8 | 0 |
| 16 | 5 | daily × 5 | 13 | 0 |
| 16 | 5 | daily × 5 | 29 | 0 |
| 32 | 5 | daily × 5 | 62 | 0 |
| 64 | 5 | daily × 5 | 72 | 0 |
| 128 | 5 | daily × 5 | >1200 | 4 |
| 125 | 10 | daily × 5 | >1200* | 9 |
| 200 | 10 | daily × 5 | >1200* | 9 |

Figure 3:
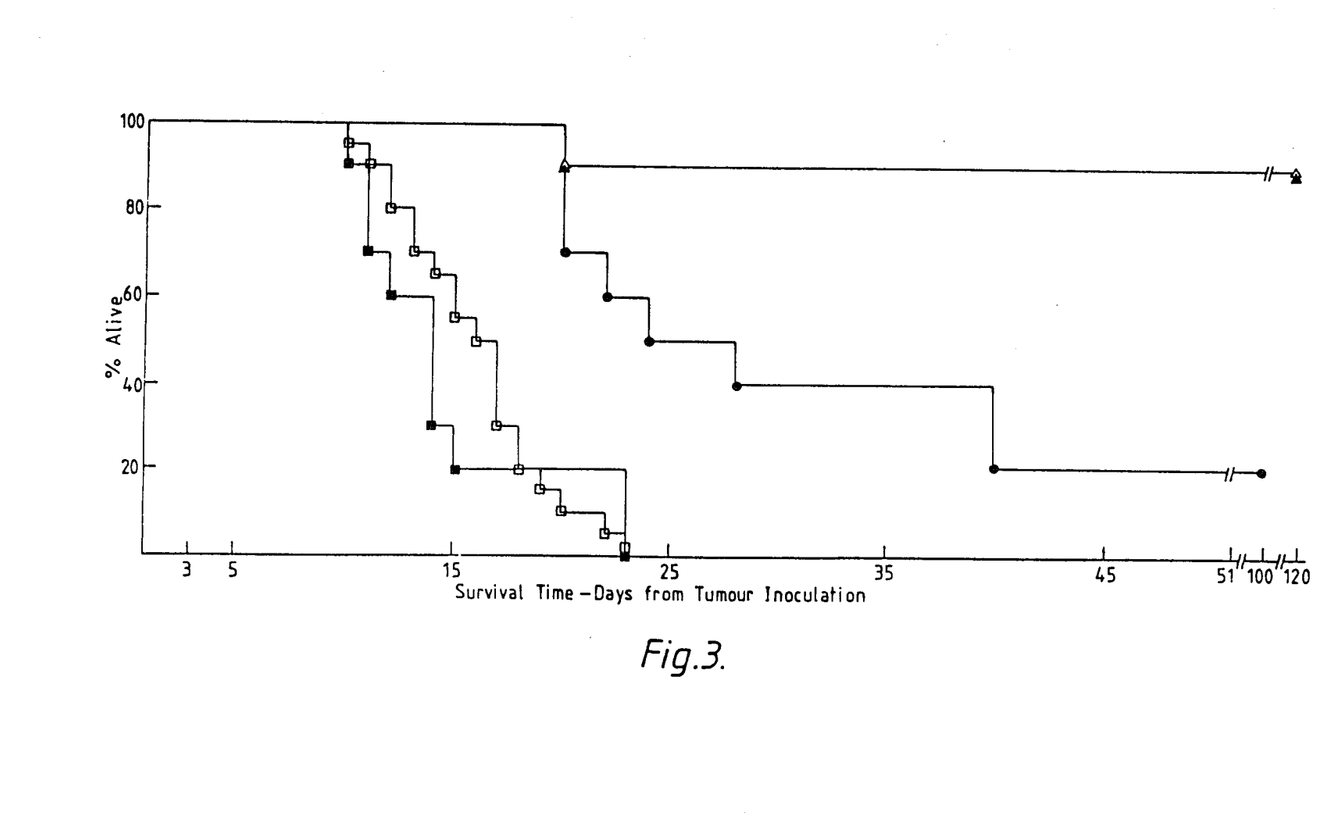

*see FIG. 3

FIG. 3 illustrates the survival of L1210 bearing mice injected with CB 3717.

■ No treatment (10 animals)-MTX control

□ No treatment (20 animals)-CB 3717 control
(Animals were injected with 20 mM NaHCO₃ buffer 0.4 ml daily×5 days.

● MTX 3 mg/kg daily×5 (10 animals)

▲CB 3717 125 mg/kg daily×5 (10 animals)

△CB 3717 200 mg/kg daily×5 (10 animals)

The difference in the survival of CB 3717 and MTX treated animals is highly significant, p<0.001 using the log rank test.

Single doses of compound CB 3717 up to 160 mg/Kg were not toxic and produced very little therapeutic effect. A 5 daily dose schedule produced increases in mean survival time which were dose related (see Table 3). At doses of 125 and 200 mg/kg 9 out of 10 long term survivors (>120 days) were seen (see FIG. 3).

Drug availability and solubility precluded the use of higher doses. As the injection solutions could only be neutralised to pH 8.5 while preserving solubility, the appropriate controls were injected with bicarbonate at pH 8.5. None of the control groups showed any increase in life span. For comparative purposes further groups of animals were treated with various doses of methotrexate, given on the same schedule. The optimal dose of methotrexate, 3 mg/kg, gave an increase in median lifespan of 71% but only 2/10 long term survivors.

Figure 4:
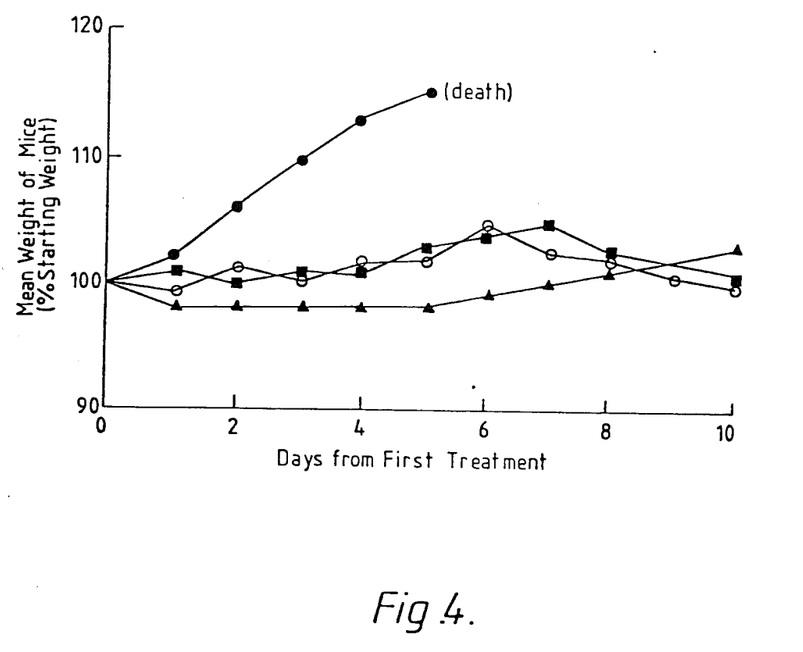

These animals did not lose a significant amount of weight or show other signs of toxicity while undergoing treatment with the drug as is illustrated in FIG. 4 of the accompanying drawings which shows body weight changes in groups of 10 mice treated with 5 daily doses of CB 3717 at 125 mg/kg/day ■ : 200 mg/kg/day (▲); untreated tumour-bearing controls (●); untreated controls without tumour (o).

The results of the tests involving treatment of L1210 tumour-bearing animals show a remarkable increase in the long term survival as compared with animals treated optimally with methotrextate.

We claim:

1. A pharmaceutical composition useful for aiding regression and palliation of cancer, comprising an effective amount of an active compound in association with a pharmaceutically acceptable carrier or diluent wherein the active compound is a compound of formula:

wherein

R represents a straight or branched chain unsaturated $C_2$-$C_4$ hydrocarbon group or a fluorine-substituted straight or branched chain hydrocarbon group having up to 4 carbon atoms;

n is 0, 1 or 2;

X, which is linked in a position ortho to the —CO—Y group, represents a halogeno or $C_1$-$C_4$ alkyl group, and where two X's are present these may be the same or different; and Y represents a group of formula:

or wherein m is an integer of 1–9 (poly-L-glutamates); or a pharmaceutically acceptable salt or ester thereof.

2. A composition according to claim 1 wherein R is allyl or propargyl.

3. A composition according to claim 1 wherein n is 1 and X is chloro or methyl.

4. A composition according to claim 1 wherein Y is an L-glutamic acid residue, one or both of the acid groups optionally being in salt or ester form.

5. A composition according to claim 1 wherein the active compound is

N-(4-(N-((2-amino-4-hydroxy-6-quinazolinyl)methyl)prop-2-ynylamino)benzoyl)-L-glutamic acid, N-(2-methyl-4-(N-((2-amino-4-hydroxy-6-quinazolinyl)methyl)prop-2-ynylamino)benzoyl)-L-glutamic acid, N-(2-chloro-4-(N-((2-amino-4-hydroxy-6-quinazolinyl)-methyl)prop-2-ynylamino)benzoyl)-L-glutamic acid.

6. A composition according to claim 1 wherein the active compound is in the form of a disodium salt or diethyl ester.

7. A compound according to claim 1 wherein R represents a 2-fluoroethyl group or a 2,2,2-trifluoromethyl group.

8. A method of aiding regression and palliation of cancer in a host which comprises administering to that host an effective amount of an active compound as defined in claim 1.

9. A method according to claim 8 wherein the active compound is as defined in any one of claims 3 to 7.

10. A compound of the formula (I)

wherein

$R^1$ is a fluorine substituted straight or branched chain hydrocarbon group having up to 4 carbon atoms, n is 0, 1 or 2;

X, which is linked in a position ortho to the —CO—Y group, represents a halogeno or $C_1$–$C_4$ alkyl group, and where two X's are present these may be the same or different; and Y represents a group of formula:

wherein m is an integer of 1–9 (poly-L-glutamates); or a pharmaceutically acceptable salt or ester thereof.

11. A compound according to claim 10 wherein n is 1 and X is chloro or methyl.

12. A compound according to claim 10 wherein Y is an L-glutamic acid residue, one or both of the acid groups optionally being in salt or ester form.

13. A compound according to claim 10 in the form of a disodium salt or diethyl ester.

14. A compound according to claim 10 wherein $R^1$ represents a 2-fluoroethyl group or a 2,2,2-trifluoroethyl group.

15. N-(4-(N-((2-amino-4-hydroxy-6-quinazolinyl)methyl)-2-fluoroethylamino)benzoyl)-L-glutamic acid.

* * * * *